(12) United States Patent
Kühn et al.

(10) Patent No.: US 9,365,306 B2
(45) Date of Patent: Jun. 14, 2016

(54) PACKAGING SYSTEM FOR MULTI-COMPONENT MEDICAL PRODUCTS

(75) Inventors: Bernd Kühn, Frankfurt am Main (DE); Werner Seiferlein, Frankfurt am Main (DE)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 608 days.

(21) Appl. No.: 13/818,839

(22) PCT Filed: Aug. 24, 2011

(86) PCT No.: PCT/EP2011/064504
§ 371 (c)(1),
(2), (4) Date: Feb. 25, 2013

(87) PCT Pub. No.: WO2012/025549
PCT Pub. Date: Mar. 1, 2012

(65) Prior Publication Data
US 2013/0152510 A1 Jun. 20, 2013

Related U.S. Application Data

(60) Provisional application No. 61/377,579, filed on Aug. 27, 2010.

(30) Foreign Application Priority Data

Oct. 8, 2010 (EP) .................................. 10186923

(51) Int. Cl.
*B65B 5/06* (2006.01)
*B65B 31/00* (2006.01)
(Continued)

(52) U.S. Cl.
CPC ............... *B65B 5/068* (2013.01); *A61M 5/002* (2013.01); *B65B 5/06* (2013.01); *B65B 31/00* (2013.01);
(Continued)

(58) Field of Classification Search
CPC ........ B65B 3/003; B65B 3/006; B65B 31/00; B65B 31/02; B65B 31/025; B65B 5/06; B65B 5/068; B65B 29/00; B65B 29/10; A61M 5/002; A61M 5/003; B65D 25/10–25/108; B65D 71/70; G21F 5/018
USPC ............ 53/50, 425, 426, 443, 449, 467–469, 53/471, 492; 206/366
See application file for complete search history.

(56) References Cited

U.S. PATENT DOCUMENTS 2,503,147 A * 4/1950 Applezweig ............ B65B 3/003
141/178
3,114,455 A * 12/1963 Stagg .................. A61M 5/3202
206/366
(Continued)

FOREIGN PATENT DOCUMENTS

EP 0790063 8/1997
FR 1300356 8/1962
(Continued)

OTHER PUBLICATIONS

Chinese Office Action issued for CN App. No. 201180051847.7, dated Jul. 31, 2014.
(Continued)

*Primary Examiner* — Stephen F Gerrity
*Assistant Examiner* — Joshua Kotis
(74) *Attorney, Agent, or Firm* — McDonnell Boehnen Hulbert & Berghoff LLP

(57) ABSTRACT

A sterile packaging system for use in the manufacture and sale of combination medical product preferably one that is attachable to an injection system to co-deliver at least two medicaments is disclosed where a tray grid comprises sterile receptacles that are removably connected, sealable and configured for use in an automated drug filling and assembly line.

9 Claims, 14 Drawing Sheets

(51) Int. Cl.
*B65B 55/02* (2006.01)
*A61M 5/00* (2006.01)
*B65D 25/10* (2006.01)
*B65D 71/70* (2006.01)
*B65D 75/52* (2006.01)
*B65B 29/00* (2006.01)
*B65B 3/00* (2006.01)

(52) U.S. Cl.
CPC .............. *B65B 55/02* (2013.01); *B65D 25/108* (2013.01); *B65D 71/70* (2013.01); *B65D 75/527* (2013.01); *B65B 3/003* (2013.01); *B65B 29/00* (2013.01); *B65B 2220/14* (2013.01); *B65B 2220/16* (2013.01)

(56) References Cited

U.S. PATENT DOCUMENTS

| | | | | |
|---|---|---|---|---|
| 3,643,812 | A * | 2/1972 | Mander | B01L 9/06 206/443 |
| 4,444,310 | A * | 4/1984 | Odell | A61B 19/0271 206/363 |
| 4,753,345 | A * | 6/1988 | Goodsir | A61M 5/008 206/365 |
| 4,867,315 | A * | 9/1989 | Baldwin | B65B 3/003 206/558 |
| 5,579,929 | A * | 12/1996 | Schwartz | B01L 9/06 206/446 |
| 6,164,044 | A * | 12/2000 | Porfano | B65B 55/10 422/28 |
| 6,305,541 | B1 * | 10/2001 | Tanner | A61M 5/002 206/366 |
| 6,802,828 | B2 * | 10/2004 | Reynolds | A61J 1/062 604/199 |
| 6,883,222 | B2 * | 4/2005 | Landau | A61L 2/081 29/469 |
| 6,913,592 | B2 * | 7/2005 | Parsons | A61M 5/30 604/218 |
| 7,100,768 | B2 * | 9/2006 | Grimard | A61L 2/183 206/438 |
| 7,169,361 | B2 * | 1/2007 | Arnold, Jr. | B01L 9/543 206/562 |
| 7,232,038 | B2 * | 6/2007 | Whitney | B01L 9/06 211/74 |
| 8,286,791 | B2 * | 10/2012 | Finke | A61M 5/008 206/366 |
| 2005/0194059 | A1 * | 9/2005 | Py | B65B 3/003 141/18 |
| 2005/0226763 | A1 * | 10/2005 | Raynal-Olive | A61L 2/208 422/28 |
| 2006/0054523 | A1 * | 3/2006 | Porret | A61L 2/08 206/439 |
| 2006/0178644 | A1 * | 8/2006 | Reynolds | A61J 1/2093 604/232 |
| 2006/0213793 | A1 * | 9/2006 | Brand | A61M 5/3205 206/366 |
| 2007/0289884 | A1 * | 12/2007 | Py | A61J 7/0053 206/221 |
| 2009/0100802 | A1 * | 4/2009 | Bush | A61M 5/002 53/434 |
| 2009/0202608 | A1 * | 8/2009 | Alessi | A61K 9/0004 424/424 |
| 2009/0288977 | A1 * | 11/2009 | Vanderbush | A61M 5/002 206/524.8 |
| 2010/0012546 | A1 * | 1/2010 | Togashi | A61B 19/026 206/534.1 |
| 2010/0262074 | A1 * | 10/2010 | Seiferlein | A61J 1/062 604/89 |
| 2011/0094188 | A1 * | 4/2011 | Bottger | A61J 1/2093 53/425 |
| 2012/0080341 | A1 * | 4/2012 | Finke | A61M 5/008 206/366 |
| 2012/0118777 | A1 * | 5/2012 | Kakiuchi | A61M 5/002 206/366 |
| 2013/0341849 | A1 * | 12/2013 | Shimazaki | A61M 5/002 269/287 |

FOREIGN PATENT DOCUMENTS

| | | |
|---|---|---|
| JP | 6321268 | 11/1994 |
| WO | 01/76664 | 10/2001 |

OTHER PUBLICATIONS

International Preliminary Report on Patentability for Int. App. No. PCT/EP2011/064504, mailed Mar. 14, 2013.

International Search Report and Written Opinion for Int. App. No. PCT/EP2011/064504, completed Jan. 4, 2012.

* cited by examiner

PACKAGING SYSTEM FOR MULTI-COMPONENT MEDICAL PRODUCTS

CROSS REFERENCE TO RELATED APPLICATIONS

The present application is a U.S. National Phase Application pursuant to 35 U.S.C. §371 of International Application No. PCT/EP2011/064504 filed Aug. 24, 2011, which claims priority to U.S. Provisional Patent Application No. 61/377,579 filed Aug. 27, 2010 and European Patent Application No. 10186923.8 filed Oct. 8, 2010. The entire disclosure contents of these applications are herewith incorporated by reference into the present application.

FIELD OF INVENTION

Specific embodiments of this disclosure relate to a packaging or tray system used in the manufacture and sale of medical products that are constructed and/or assembled from multiple components (combination of medicament and medical device), such as a medicated module for medical delivery devices, specifically such devices intended for delivering at least two drug agents from separate reservoirs using a device having only a single dose setting mechanism and a single dispense interface, wherein one drug is contained in the packaging. A single delivery procedure initiated by the user of the delivery device may cause a non-user settable dose of a second drug agent and a variable set dose of a first drug agent to be delivered to the patient. This second drug agent may be contained within the medicated module, which is contained within the packaging system of the present disclosure. The present disclosure is of particular benefit because sterility of the medicated module during filling with the drug agent and sealing of the medicated module may be maintained during the entire manufacturing process. In addition, the disclosure may lead to a cost effective manufacturing process by minimizing the number of process steps and the amount of sterile packaging materials required for the final drug product.

BACKGROUND

Certain disease states require treatment using one or more different medicaments. Some drug compounds need to be delivered in a specific relationship with each other in order to deliver the optimum therapeutic dose. The present disclosure is of particular benefit where combination therapy is desirable, but not possible in a single formulation for reasons such as, but not limited to, stability, compromised therapeutic performance and toxicology.

For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogues) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it may be advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient up to a "maintenance" dose. A further example would be if one active requires a non-adjustable fixed dose while the other one is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or to make the necessary accurate calculation of the required dose combination. This is especially true for users with dexterity or computational difficulties. In some circumstances it is also necessary to perform a priming procedure of the device and/or the needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The above-mentioned problems may be overcome by providing separate storage containers for two or more active drug agents that are then only combined and/or delivered to the patient during a single delivery procedure. In particular, the use of a medicated module containing a single dose of medicament must be separately manufactured for use with a primary drug delivery device. The present disclosure provides a packaging, container, or tray system that preserves the sterility of partially assembled and finished medicated modules containing a secondary medicament from the beginning of manufacture through to attachment by the user to a delivery device containing a primary medicament.

These and other advantages will become evident from the following more detailed description of the invention.

One problem to be solved by the present invention is to provide a packaging system and a method where the safety of the user is increased.

SUMMARY

The present disclosure comprises a packaging system to allow efficient and cost effective manufacturing of medical products or devices that are assembled from multiple components. One such multi-component medical device may comprise a medicated module. The medicated module may be designed for use with a drug delivery system, such as an injection device, containing a first medicament. The medicated module may contain a second medicament and, when attached to a primary drug delivery system, it may allow the user to deliver a complex combination of multiple drug compounds within a single drug delivery system with one activation step. The packaging system may be configured to enter the manufacturing and/or assembling process as a sterile tray grid of receptacles containing at least one sub-assembly of the particular medical product, e.g. of the medicated module, to be assembled into a finished product for sale. During the assembly process, additional components can be added to the at least one sub-assembly until eventually a completed multi-component medical product, e.g. the medicated module, is constructed. During the assembling process, drugs or other substances can be added to the at least one sub-assembly or to other components that comprise the medical product. Exiting from the manufacturing/assembling process there are sealed sterile packages containing a predetermined number of receptacles, each of which holds a finished, ready-to-use, multi-component medical product ready for distribution to and use by a care giver or patient.

The present disclosure may minimize waste from the manufacturing process because only outer protective sleeves of the incoming trays and a cover seal of the tray itself need to be disposed. The tray may be carried through the entire manufacturing process. Portions of the tray containing finished medicated modules may be ultimately commercially packaged for distribution to end users. In particular, the sterile tray grid of receptacles may be configured to be portioned into end user grids. Furthermore, the sterile tray grid may be configured to be placed in commercial packaging. Thus, the overall manufacturing process can be designed more efficient and less complex. The packaging system of the trays may be configured and fabricated of materials to withstand high-speed/high throughput manufacturing and enables the efficient filling of multiple sub-assemblies of modules in a single instance because each receptacle in the grid of the tray system contains a module sub-assembly. Each sub-assembly in the tray system may be exactly positioned for automated filling through the use of a centering member located in each receptacle. The single tray system may allow for cost effective industrial scale manufacturing through automated systems using established manufacturing principles. The tray system according to the present disclosure hence may be for use during manufacturing of multi-component medical products as well as for end user and/or commercial packaging. The tray system may comprise features configured for holding the units or sub assemblies in precise position for manufacturing steps such as assembly and filling, e.g., and may further comprise features to enable being suitable for final packaging of individual units.

One aspect relates to a packaging system. The packaging system may be for use during the manufacturing of multi-component medical products, e.g. of medicated modules. Furthermore, the packaging system may be suited for holding the completed multi-component medical products. The packaging system may comprise a sterile tray grid. The tray grid may be square. The tray grid may comprise at least two receptacles. Preferably, the tray grid comprises a plurality of receptacles. The receptacles may be connected, preferably releasably, connected. Each receptacle may have a top sealing surface. Each receptacle may have an internal chamber. The internal chamber may have a centering member. The centering member may be configured to support one sub-assembly of a multi-component medical product. The centering member may be configured to support two or more sub-assemblies of a multi-component medical product. The two or more sub-assemblies may form a respective multi-component medical product, e.g. a medicated module.

Each receptacle may be removably connected to an adjacent receptacle. In particular, each receptacle may be, preferably removably, connected to an adjacent receptacle through a strike line. The strike line may be a perforation.

The grid comprises an array of receptacles releasably connected to each other, preferably through the strike line. This strike line allows the user to break-off, or snap-off, or otherwise cut one or more receptacles at a time from the array by bending back or tearing off one or more receptacles from the array. In some cases, the strike line can be an actual perforation that outlines one or more receptacles. Each receptacle also preferably has the folding edge that may allow the user to remove the sealing structure covering the interior chamber. Removal of the seal may allow access and removal of the finished medicated module. The trays can also be designed for use as the final packaging of the filled medicated needle.

According to an embodiment, the sterile tray grid comprises 2 to 400 receptacles. The sterile tray grid may comprise 7 to 210 receptacles. Preferably, the sterile tray grid comprises 7 to 28 receptacles.

Preferably, the selection of the initial grid size (i.e. the number of connected receptacles) is determined from a study of the manufacturing equipment that will be used to fill, assemble, and seal the medicated module. Grid sizes can range from 2×1 units to 10×40 units or 2 to 400 receptacles. Most preferably, a grid size of 7×10 units or 14×10 units is best. Other grid arrangements leading to the same number of connected units may be possible and within the scope of the present disclosure.

According to an embodiment, multiple sterile tray grids are stacked on each other.

According to an embodiment, each receptacle has a folding edge. The folding edge may be configured to allow a user to remove a sealing structure covering the interior chamber. Each receptacle may have a bottom sealing surface.

According, to an embodiment, the internal chamber is configured to temporarily accept a portion of an automated drug filling machine.

According to an embodiment, each receptacle is molded with a plastic. The plastic may have sufficient rigidity for processing through an automated drug filling and assembly line. Additionally or alternatively, each receptacle may be molded with a plastic that can be sterilized with gamma rays. Additionally or alternatively, each receptacle may be molded with a plastic that can be sterilized with ethylene-oxide.

The grid can be manufactured of any type of material that can be sterilized, for example, using gamma-rays, ethylene-oxide, $H_2O_2$, electron beam, or the like. To minimize the cost and to allow for easy recycling, preferably the grid is molded from one or more plastic materials, most preferably from the plastics selected from the group consisting of polyolefines (polypropylene, polyethylene, polyisobutylene, polybutylene and the like), polystyrene, polyester, polyethylene-terephthalate, polyamides and mixtures or laminates thereof. The grid can be manufactured using deep-drawing or injection-molding techniques.

According to an embodiment, each receptacle contains the sub-assembly for the multi-component medical product. The sub-assembly may be supported by the centering member. The sub-assembly may be fixed against movement with respect to the receptacle, in particular fixed against rotational movement. The sub-assembly may be fixed against movement by means of the centering member. The centering element may be configured for positioning the medical product or at least one sub-assembly thereof in the receptacle in a precise position and fix it against movement. Holding the sub-assembly in a precise position would provide for automated manufacturing and assembly steps using the tray system on high-speed manufacturing equipment. For example, a second sub-assembly could be mounted on or connected to the first sub-assembly wherein the centering element positions and fixes the first sub-assembly against movement. Elements of the manufacturing equipment so can interact with the sub-assembly contained in the receptacle for multiple manufacturing steps like filling and assembly. A preferred high-speed manufacturing equipment would process 60-200 units per minute.

According to an embodiment, the top sealing surface is bonded to a removable seal. The grid may be wrapped in a removable secondary seal.

According to an embodiment, each receptacle contains a finished multi-component medical product, e.g. a finished medicated module. In this embodiment, the top sealing surface of each receptacle may be bonded to removable seal, as well. The removable seal may have perforations outlining each receptacle.

A further aspect relates to a packaging system. The packaging system may comprise a sterile tray grid of 2 to 400, preferably 7 to 210, most preferred 7 to 28 connected receptacles. Each receptacle may have a top sealing surface. Each receptacle may have a folding edge. Each receptacle may have an internal chamber. The internal chamber may have a centering member. Each receptacle may have a finished medicated module in the internal chamber. The finished medicated module may be positioned on the centering member. Each receptacle may have a seal. The seal may be bonded to the top sealing surface. Each receptacle may be, preferably removably, connected to an adjacent receptacle. The respective receptacle may be connected to the adjacent receptacle through a strike line.

According to an embodiment, the medicated module contains a secondary medicament, preferably a single dose of the secondary medicament. The secondary medicament may be liquid. The medicated module may contain a drug dispense interface, e.g. a needle. The medicated module may be attachable, preferably releasably attachable, to a drug delivery device. The drug delivery device may contain a primary medicament, preferably a plurality of doses of the primary medicament.

According to an embodiment, the secondary medicament comprises a GLP-1. Alternatively, the secondary medicament may comprise a premix of insulin and a GLP-1.

The trays are segmented or partitioned to provide a number of receptacles in a row, and a number of rows in parallel that fit with the later arrangement of the number of medicated devices or needles to be supplied to the patient or user. In order to facilitate tearing off the foil or seal that maintains the sterility of each finished medicated module, the folding edge is included on each receptacle. This folding edge may be on the top or bottom of the receptacle. Each receptacle may be configured to hold the fully assembled and filled medicated module in the interior chamber that is preferably formed during the fabrication of the starting grid. Initially, however, the receptacles of the starting grid may hold only the sub-assembly of the medicated module, preferably without the second medicament. The interior chamber may have the centering member configured to hold or position the sub-assembly in predefined vertical position to allow accurate filling of the secondary medicament and sealing or connecting of a second sub-assembly to form the complete finished medicated module. The centering member may comprise an annulus, a shelf or a rib or may be a molded section configured to form fit part of the sub-assembly. Regardless of the actual design of the centering member, it should allow the sub-assembly to remain spatially fixed during the filling and assembly steps of an automated manufacturing line used to complete the finished medicated module. Spatially fixed would mean that the sub-assembly within the receptacle is in a fixed and precisely predetermined position to allow elements of an automated filling line to get in interaction with the sub-assembly for filling and assembly processes at high line speed of more than 100 units per minute. At any time of the manufacturing process, the position and alignment of the sub-assembly in its receptacle would be fully known and determined. Dependent on the shape of the sub-assembly and the required process step, the sub-assembly would be fixed against axial rotation to allow for assembly steps applying torque forces with rotational movement. To allow for a robust filling process, the subassembly needs to be fixed and vertically aligned with e.g. the filling needle, so tilting of the sub-assembly is to be avoided. Further, the sub-assembly may be fixed against horizontal movement out of its seat to maintain the predetermined position and interaction with machine features for assembly. The interior chamber should also be sized to accept a portion of the automated drug-filling machine that may perform a filling or assembly operation on the sub-assembly. Most preferably, the interior chamber would be configured to allow mechanized or robotic structures that will interact with the sub-assembly while it remains positioned in the internal chamber.

A further aspect relates to a method of assembling multi-component medical products using sterile tray grids. The method may comprise the step of providing a packaging system. The packaging system may comprise a sterile tray grid, e.g. a starting grid, of at least two connected receptacles. Each tray may have a top sealing surface. Each tray may have an internal chamber. The internal chamber may have a centering member. Each tray may have first sub-assembly. The first sub-assembly may be positioned on the centering member. Each receptacle may be removably connected to an adjacent receptacle. The packaging system may be entirely contained within a first seal. In a second step, the seal may be removed in a sterile environment. In next step, at least a second sub-assembly may be connected to the respective first sub-assembly. In a next step, a second seal may be attached to the sealing surfaces to form a respective finished sterile tray grid of sealed receptacles. The respective receptacle may contain a multi-component medical product.

In one step, a medicament may be added to the first sub-assembly under sterile conditions. The finished tray grid of sterile receptacles may be partitioned into end user grids and placed in commercial packaging. The end user grids may contain from 2 to 28 receptacles.

The starting grid of the tray assembly containing the sub-assemblies preferably is sterilized and can have the first seal bonded to the sealing surface of the tray. Alternatively, in some situations no seal is needed or the tray is enclosed in a protective sleeve or bag. This sealed tray system can be wrapped or covered with a second sealing means, such as a bag, a lid or the like material that can be easily removed at the start of the automated filling and assembly process once positioned in a clean room. After the sub-assembly is filled with medicament and a second sub-assembly has been connected to the original sub-assembly to complete the medicated module, a third seal is bonded to the receptacle sealing surface. This third seal is configured so that each receptacle is individually and removably sealed. A single seal material can be bonded to the grid and then perforated around each receptacle to form individual seals for each receptacle. Once the third seal is applied, the tray system can be divided or cut into smaller grid sizes to accommodate user friendly or predetermined dose specific packages. Grid sizes of from 2 receptacles to 28 receptacles may be created and separately packaged, preferably grid sizes from 7 to 14 receptacles. Each receptacle may hold the sterile, finished module containing a single dose of a secondary medicament. These smaller grid sizes are then individually packaged for distribution to the end users.

Although the present disclosure may be applicable to the manufacture/assembly of any multi-component medical product or device, one such application is in the manufacture of a medicated module, as described herein, that can be filled with a number of secondary medicaments such as insulin, insulin analogs, insulin derivatives, GLP-1 or GLP-1 analogs, analgesics, hormones, beta agonists or corticosteroids, or a combination of any of these compounds.

For the purposes of the present disclosure the term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one embodiment, the sub assembly of the medicated module preferably has a reservoir that can be filled with the secondary medicament. In a most preferred configuration, the reservoir is filled with a single dose of the medicament, preferably a liquid medicament, such as a GLP-1 or a premix of insulin and a GLP-1. The finished medicated module comprises the reservoir having the single dose of the medicament. The finished medicated module may comprise any configuration for attachment to a primary drug delivery device, such as an injection device, most preferably a pen-type injection device containing a multi-dose reservoir of primary medicament. The medicated module may comprise a housing. The housing may comprise a connector configured for attachment to the drug delivery device. The housing may comprise a proximal end and a distal end. The medicated module may comprise a first needle cannula. The first needle cannula may be positioned in the proximal end of the housing of the medicated module. The medicated module may comprise a second needle cannula. The second needle may be positioned in the distal end of the housing. The first and second needle cannulae may be in fluid communication with the reservoir holding the single dose of the medicament. The medicated module could also contain a needle guard or other safety mechanism that may cover the second needle cannula. The medicated module can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations, it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

The primary drug delivery device for use with the medicated module can be used more than once and, therefore, is multi-use, however, the drug delivery device may also be a single use disposable device. Such a device may or may not have a replaceable reservoir of the primary drug compound. It is also possible to have a suite of different medicated modules for various conditions that could be prescribed as one-off extra medication to patients already using a standard drug delivery device. Should the patient attempt to reuse a previously used medicated module, it is preferred to include a locking needle guard that is activated after drug dispense or insertion that could alert the patient to this situation. Once attached, the medicated module may allow both medicaments to be delivered via one injection needle and in one injection step. This may offer a convenient benefit to the user in terms of reduced user steps compared to administering two separate injections. This convenience benefit may also result in improved compliance with the prescribed therapy, particularly for users who find injections unpleasant or who have computational or dexterity difficulties. The medicated module may be filled with a liquid, or alternatively with a powder, suspension or slurry. In one embodiment, the medicated module could be filled with a powdered medicament that is either dissolved or entrained in the primary medicament as it is injected through the medicated module.

According to a preferred embodiment, a packaging system comprising a sterile tray grid of at least two connected receptacles is provided. Each receptacle has a top sealing surface and an internal chamber having a centering member configured to support at least one sub-assembly of a multi-component medical product.

According to a preferred embodiment, a packaging system for use during the manufacturing of multi-component medical products is provided comprising a sterile tray grid of at least 2 connected receptacles. Each receptacle has a top sealing surface and an internal chamber having a centering member configured to support one sub-assembly of a multi-component medical product, wherein each receptacle is removably connected to an adjacent receptacle.

According to a preferred embodiment, a packaging system comprising a sterile tray grid of 2 to 400, preferably 7 to 210, most preferred 7 to 28 connected receptacles, is provided where each receptacle has a top sealing surface, a folding edge, an internal chamber having a centering member, a finished medicated module in the internal chamber and positioned on the centering member and a seal bonded to the top sealing surface. Each receptacle is removably connected to an adjacent receptacle through a strike line.

According to a preferred embodiment, a method of assembling multi-component medical products using sterile tray grids is provided, the method comprising the step of providing the previously described packaging system, the packaging system being entirely contained within a seal. In a further step, the seal is removed in a sterile environment. In a further step, the at least one second sub-assembly is connected to the first sub-assembly to form a respective finished multi-component medical product. In a further step, a further seal is attached to the sealing surfaces to form a finished sterile tray grid of sealed receptacles, where the respective receptacle contains a respective multi-component medical product.

According to a preferred embodiment, a method of assembling multi-component medical products using sterile tray grids is provided, the method comprising the step of providing a packaging system comprising a sterile tray grid of at least 2 connected receptacles, where each tray has a top sealing surface, an internal chamber having a centering member, and a first sub-assembly positioned on the centering member, wherein each receptacle is removably connected to an adjacent receptacle and the packaging system is entirely contained within a first seal. The method further comprises the steps of removing the seal in a sterile environment, connecting at least a second sub-assembly to the first sub-assembly and attaching a second seal to the sealing surfaces to form a finished sterile tray grid of sealed receptacles, where each receptacle contains a finished multi-component medical product.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

The present disclosure comprises a packaging or tray system used in the filling, assembly, and packaging of any type of medical product or device that is constructed of two or more components and that must be maintained sterile through some portion of the assembly process. The following detailed description is directed to only one such possible multi-component medical product being a medicated module designed to be used with a primary drug delivery device that allows a combination of two of more medicaments to be administered to a patient. More specifically, medicated modules are used to administer a fixed predetermined dose of a secondary drug compound (medicament) along with a variable dose of a primary or first drug compound through a single output or drug dispense interface. The tray system of the present disclosure can be configured to initially hold a sub-assembly of the medicated module in a grid of removably connected receptacles and to move through a sterile filling and assembly line where the sub-assembly is filled with a medicament, the module is assembled, the receptacles are sealed and then divided up into smaller arrays for packaging and distribution to end users. Using such a system may minimize aseptic handling steps and/or removal of the medicated module from the single starting grid during the manufacturing process. However, in some circumstances it may be necessary during the manufacturing process to remove the medicated module or components thereof from the tray and to replace them back in the tray when a particular manufacturing step was finished.

Figure 1:
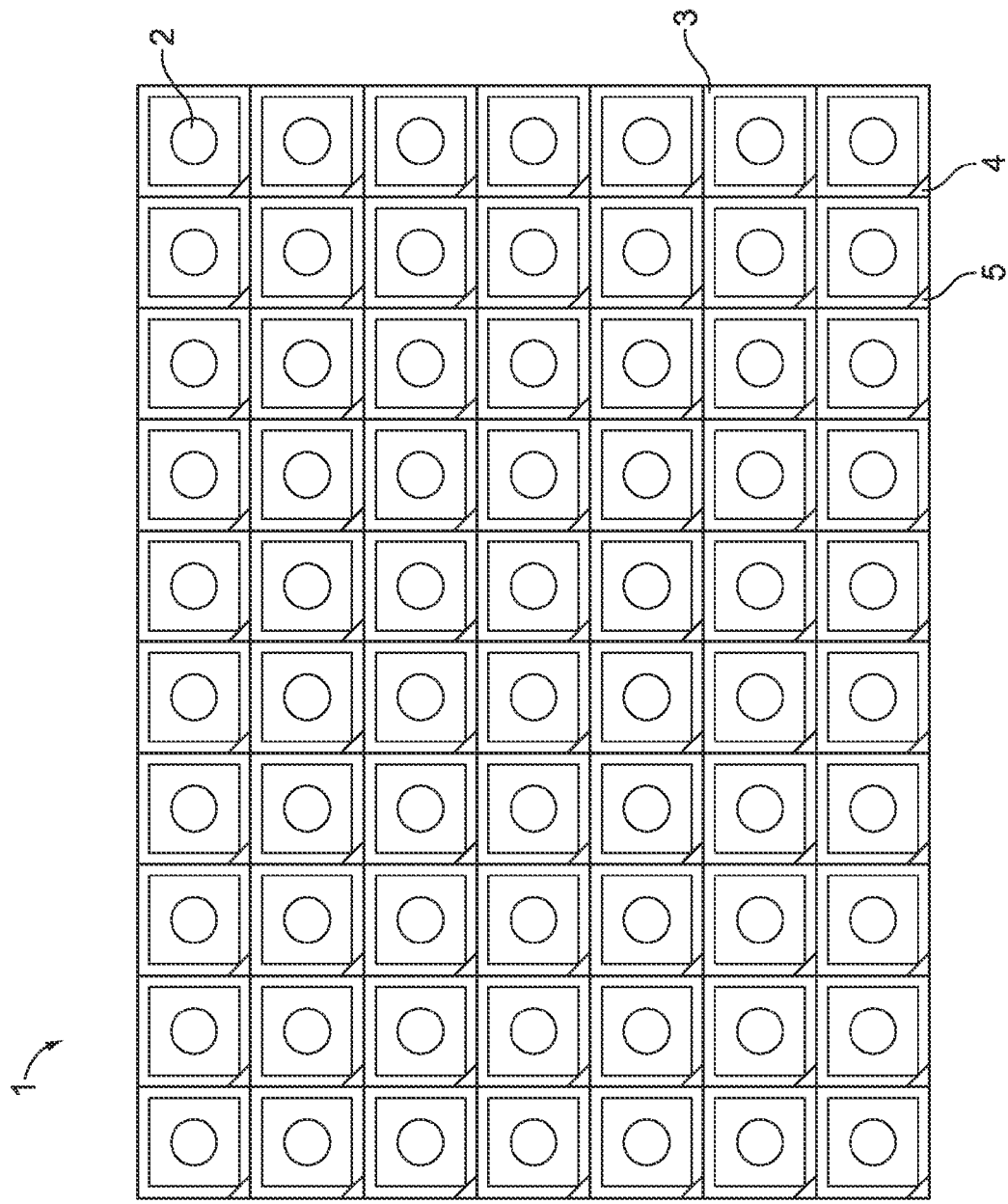
FIG. 1 illustrates a top view of one possible embodiment of the tray system.
Figure 2:
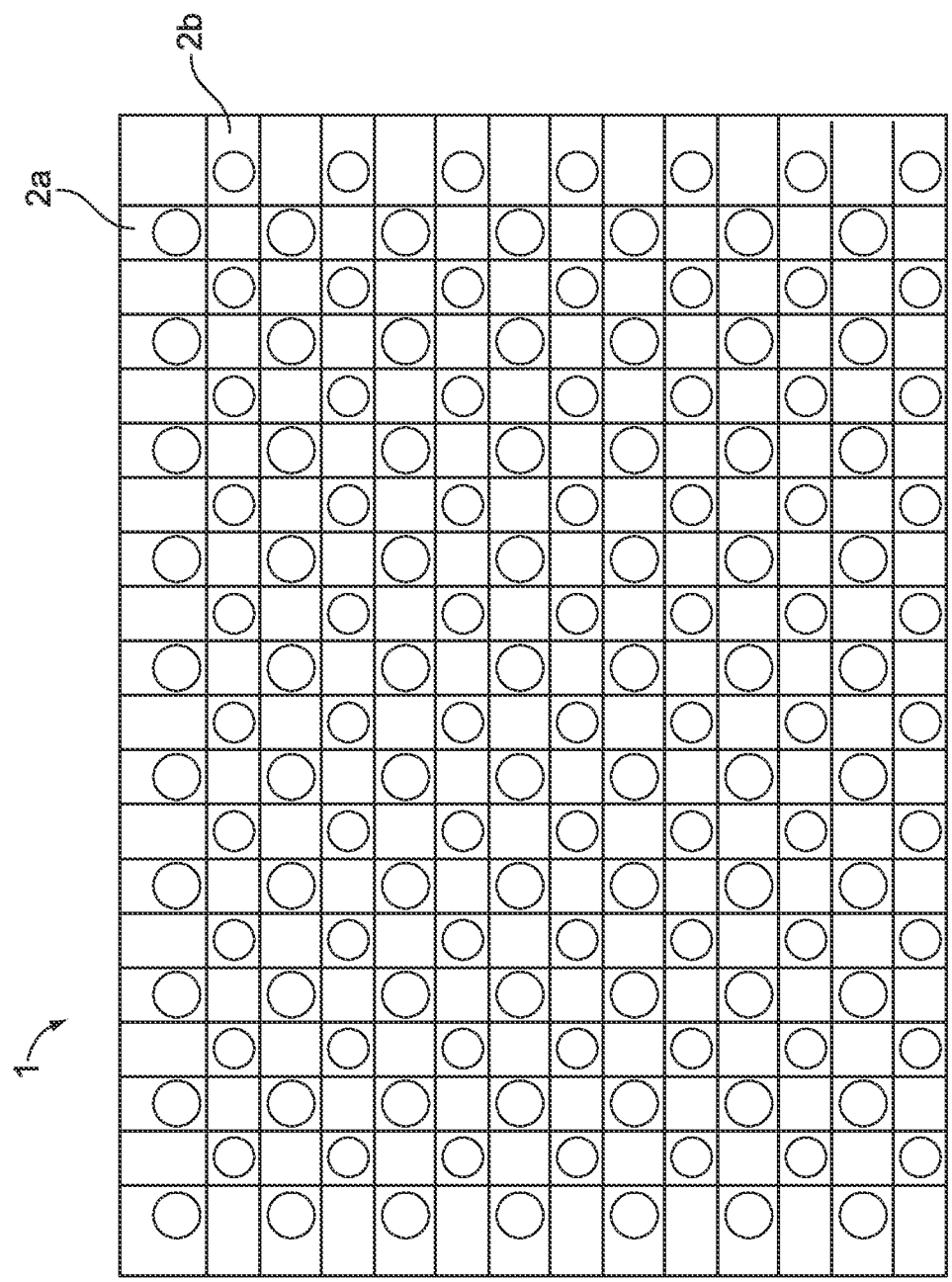
FIG. 2 illustrates a top view of another possible embodiment of the tray system holding two separate components.

FIG. 1 illustrates a top view of the starting grid or tray system 1 of receptacles 2 having a rectangular shape of 7 receptacles by 10 receptacles. Of course, the present disclosure is not limited to any particular size or shape. The present disclosure may also not be limited to a particular number of receptacles 2. Preferably the starting size and shape is selected based on the specific manufacturing equipment that will be used to fill and assemble the medicated modules contained in each receptacle or based on the desired configuration for the final user pack. The starting grid 1 contains strike lines 3. Strike lines 3 allow individual receptacles 2 to be removed and separated from one another. The starting grid 1 also contains perforations 5 that allow discrete rows containing 7 receptacles to be separated from the grid 1 for individual packaging and distribution to end users. FIG. 2 illustrates another possible tray design that holds two separate components in two distinct receptacles 2a and 2b, respectively. These two components are ultimately connected together in the assembly process to form a single medical component.

Figure 3:
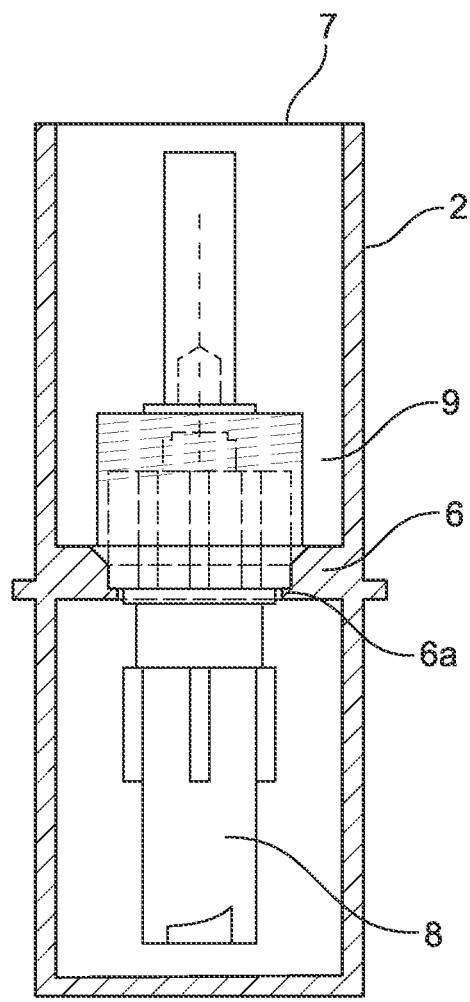
FIG. 3 illustrates a sectioned side view of an embodiment of one receptacle from the tray system containing a finished medicated module.
Figure 4:
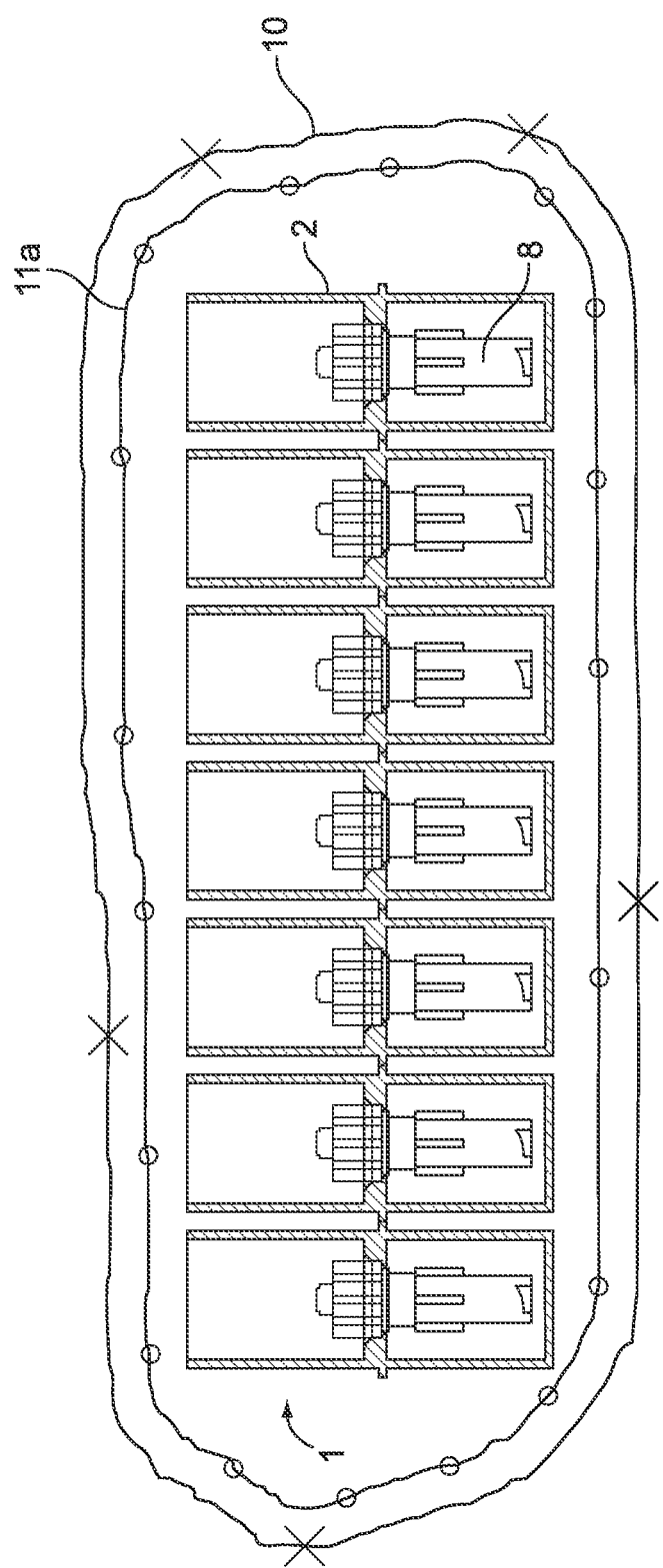
FIG. 4 illustrates a single tray with closed bottom section, positioned in a double foil bag as sterile barriers.

FIG. 3 shows a single receptacle 2 containing a fully assembled medicated module 9 positioned on a centering member 6 and aseptically enclosed by a seal 7. To avoid radial movement of a section of the module 9 during the assembly process, a form fit 6a is manufactured into the receptacle 2 that holds the component in a fixed radial position. Each receptacle 2 has a folding edge 4 (see FIG. 1) that allows the user to remove seal 7 from the top of the receptacle. Originally, receptacle 2 contained only sub-assembly 8 as best illustrated in FIG. 4.

Figure 5:
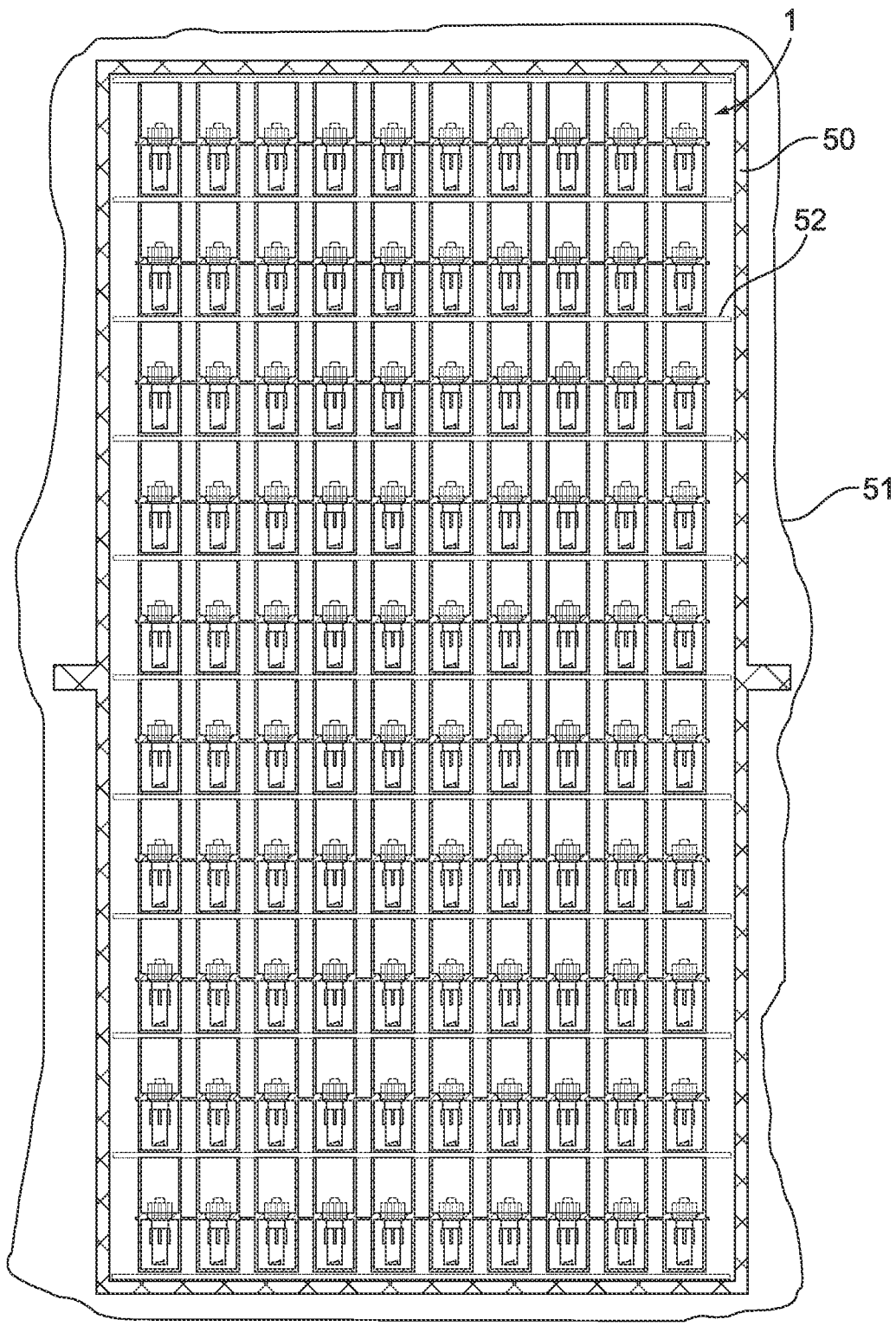
FIG. 5 illustrates a stack of 10 trays with closed bottom section, separated by protective sleeves and positioned in a protective carrier box with second protection sleeve.
Figure 6:
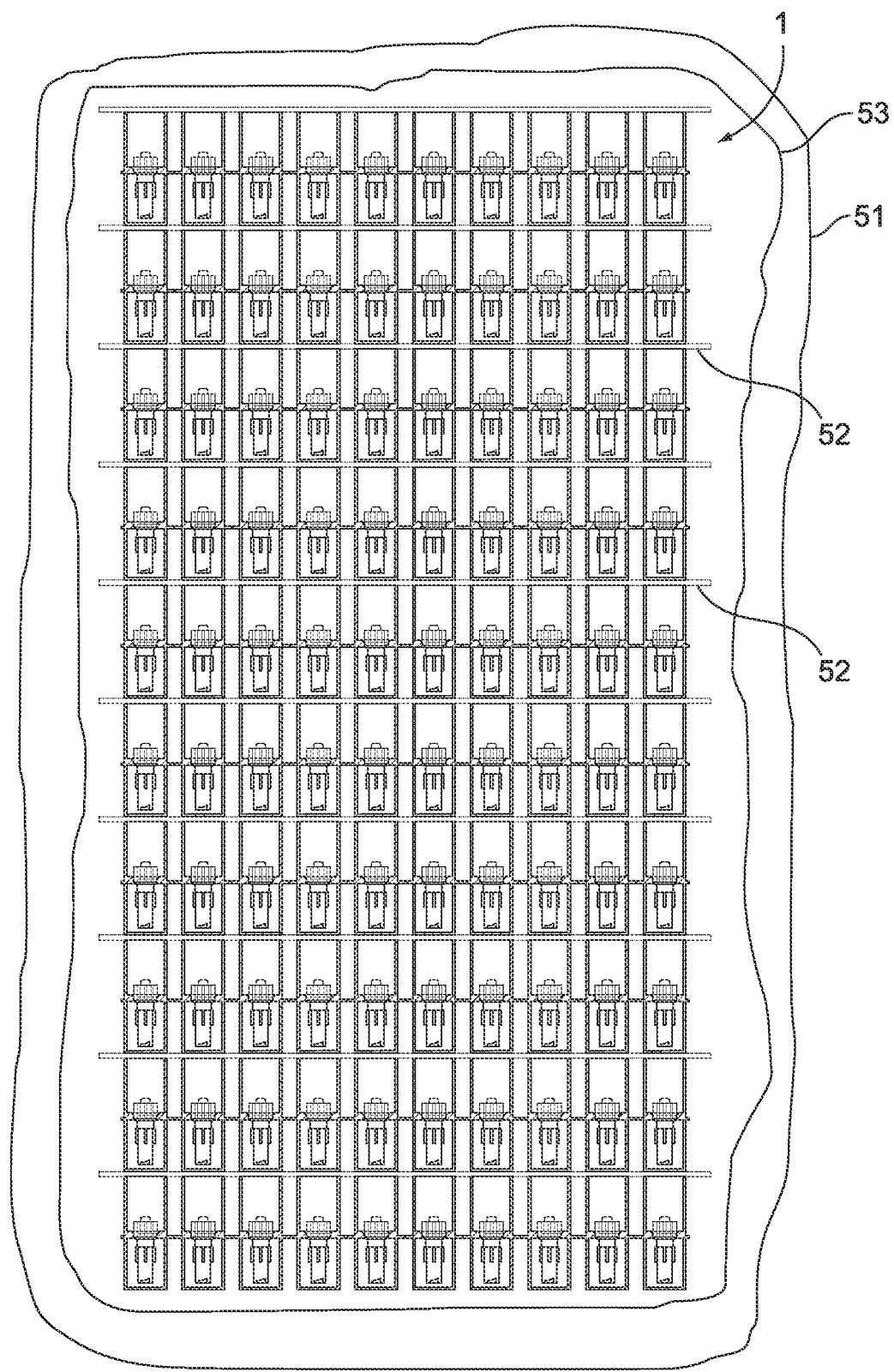
FIG. 6 illustrates a stack of 10 trays with closed bottom sections, separated by protective sleeves and positioned in a double foil bag as sterile barriers.
Figure 7:
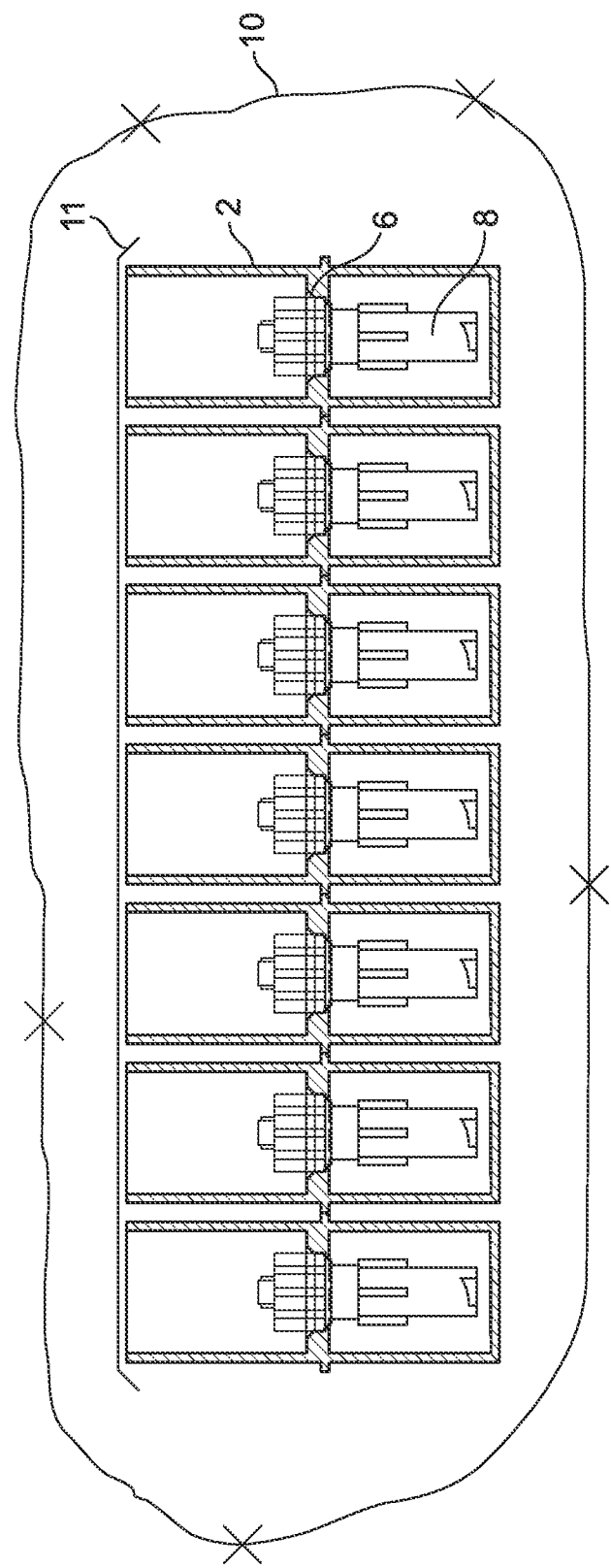
FIGS. 7-11 illustrate sectioned side views of the various configurations of the tray system as it moves through a filling and assembly line.

FIGS. 7 through 11 show one embodiment of the tray system 1 in various stages of the manufacturing process. FIG. 7 shows the grid 1 wrapped in a protective first seal 10 to maintain the sterility of the starting tray system 1. A second seal 11 covers a top opening of the receptacles 2 to maintain sterility of the component or sub-assembly 8. Alternatively, as illustrated in FIG. 4, this second seal 11 may be accomplished by a second bag 11a that is completely enclosed in the first seal 10. This starting tray system 1 would be received from the manufacturer of the medicated module sub-assemblies 8. Stacks of such tray systems 1 could be prepared and provided sterile to the manufacturing process positioned in boxes as illustrated in FIG. 5 where trays 1 are stacked with a protective sleeve 52 in between each layer when contamination risk is high and placed in a box 50. This box 50 is then sealed in bag 51. Alternatively, the box 50 can be replaced with a second protective bag 53 as shown in FIG. 6.

Figure 8:
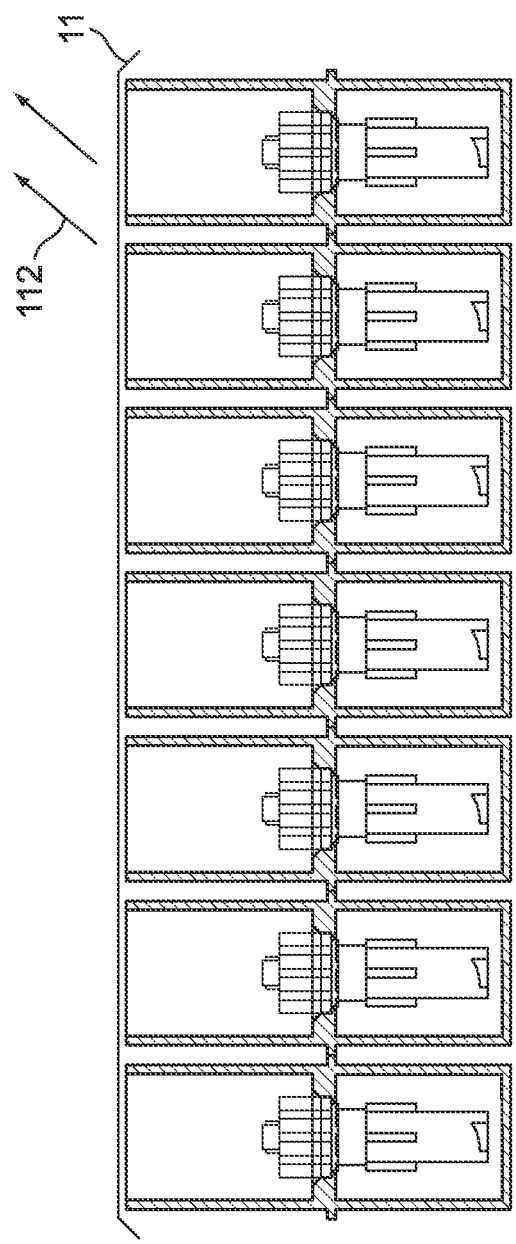

Referring again to FIG. 7, the grids 1 of receptacles 2 that are loaded with sub-assemblies 8 and enclosed with a second seal 11 are subsequently sterilized, preferably with gamma rays or ethylene-oxide. By holding each sub-assembly 8 with centering member 6, the tray system 1 can be subject to high speed/high throughput automated filling and assembly machinery that uses robotics to perform the filling and final assembly procedures. The material of construction of the grid 1 should have enough dynamic stiffness to withstand the handling of a high speed/high throughput manufacturing process. FIG. 8 shows the tray system 1 after entering a clean room, after the outer seal 10 has been removed, and immediately before the secondary seal 11 is removed in the direction of arrows 112.

Figure 9:
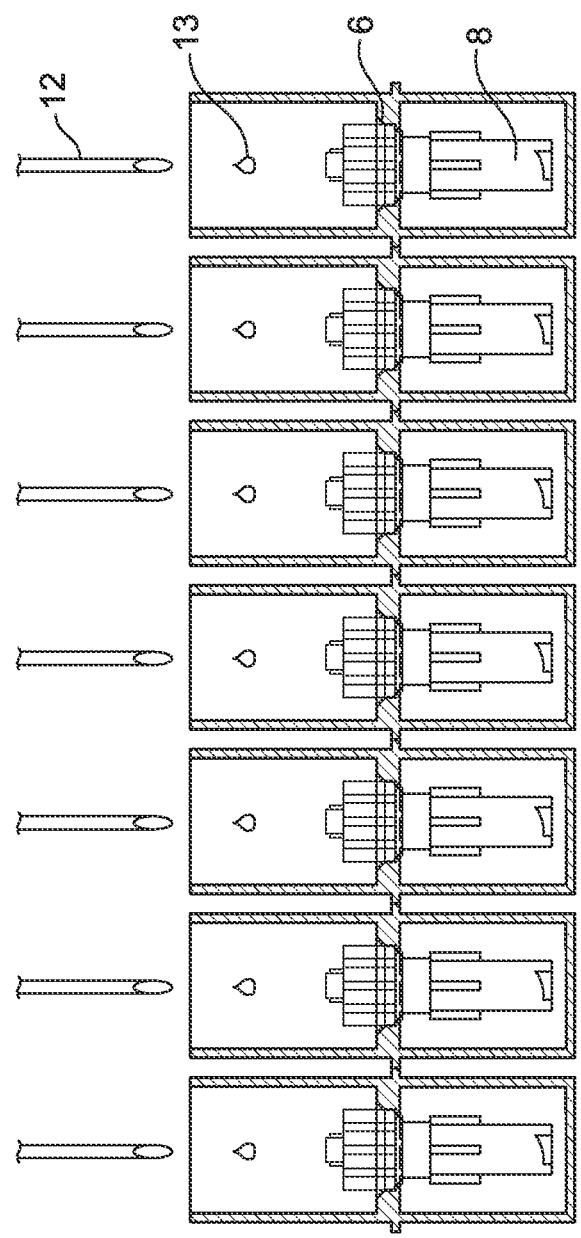
Figure 10:
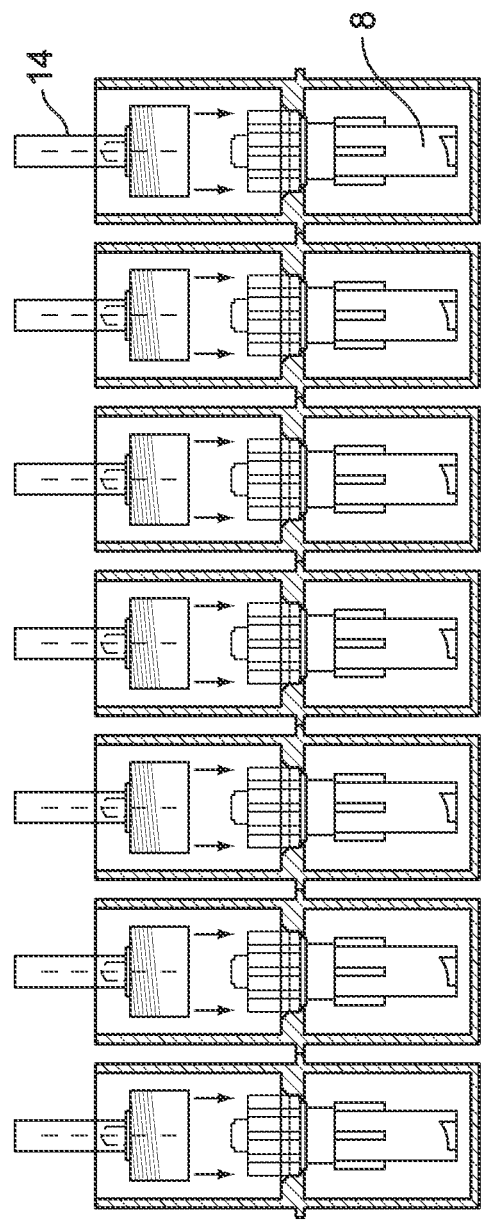
Figure 11:
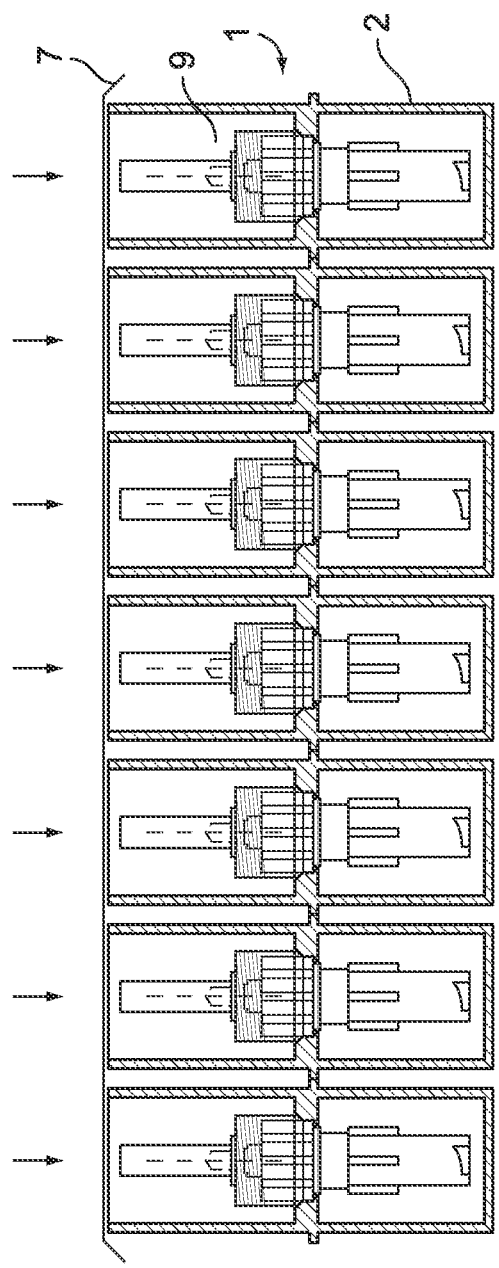
Figure 12:
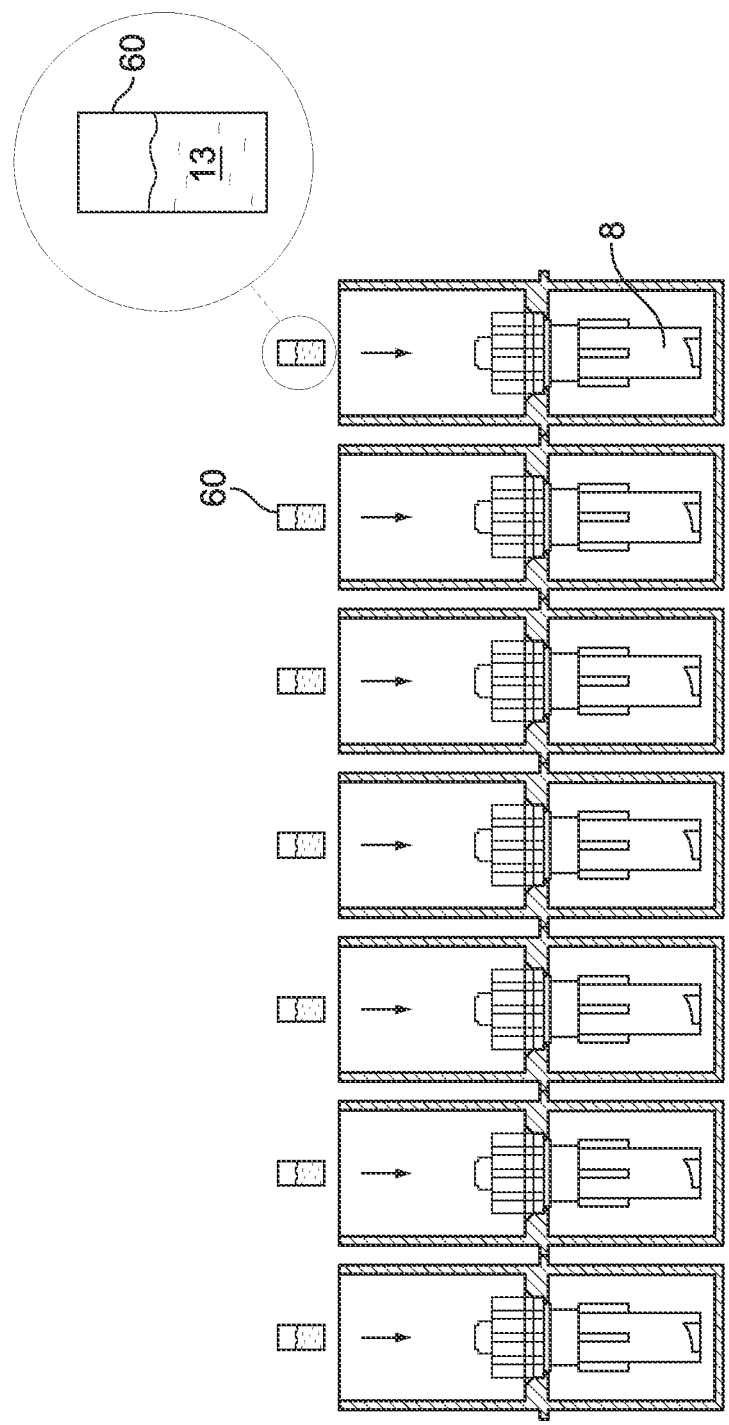
FIG. 12 illustrates the insertion process of a primary pack component filled with drug substance formulation (filled pin) into the needle sub-assembly in the tray system.
Figure 13:
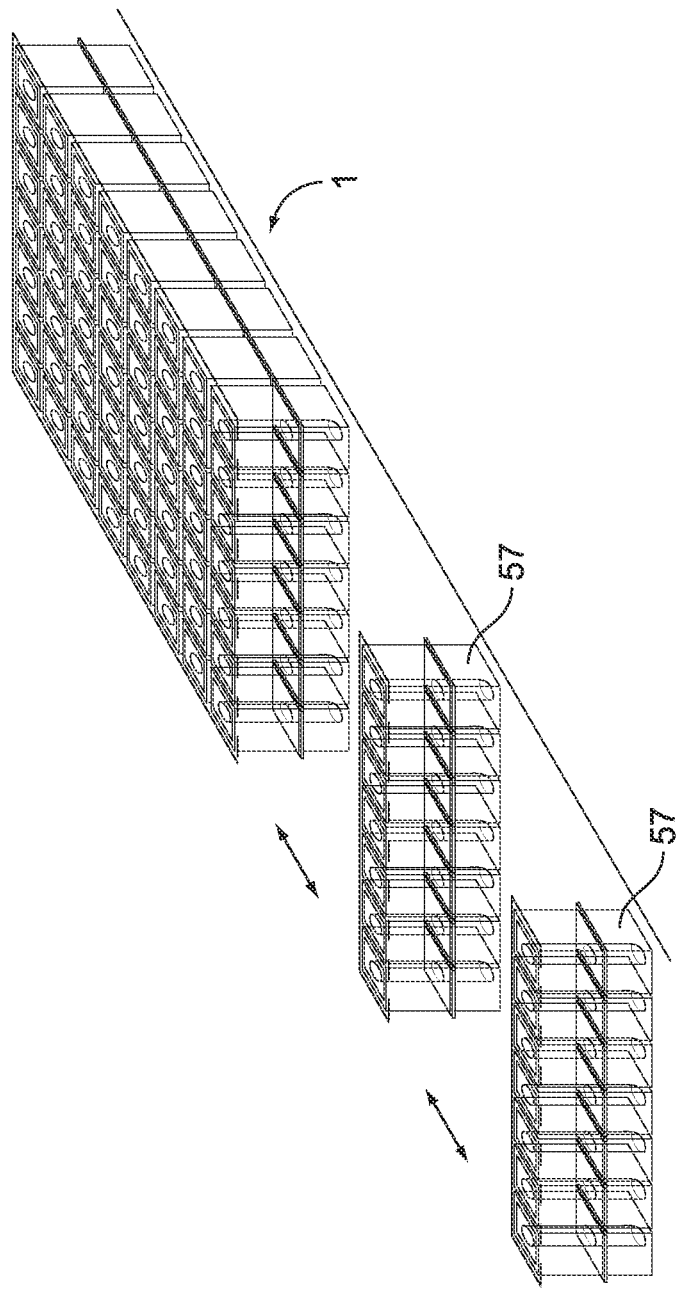
FIG. 13 illustrates the partitioning of the completed and sealed trays into packaged sized components.
Figure 14:
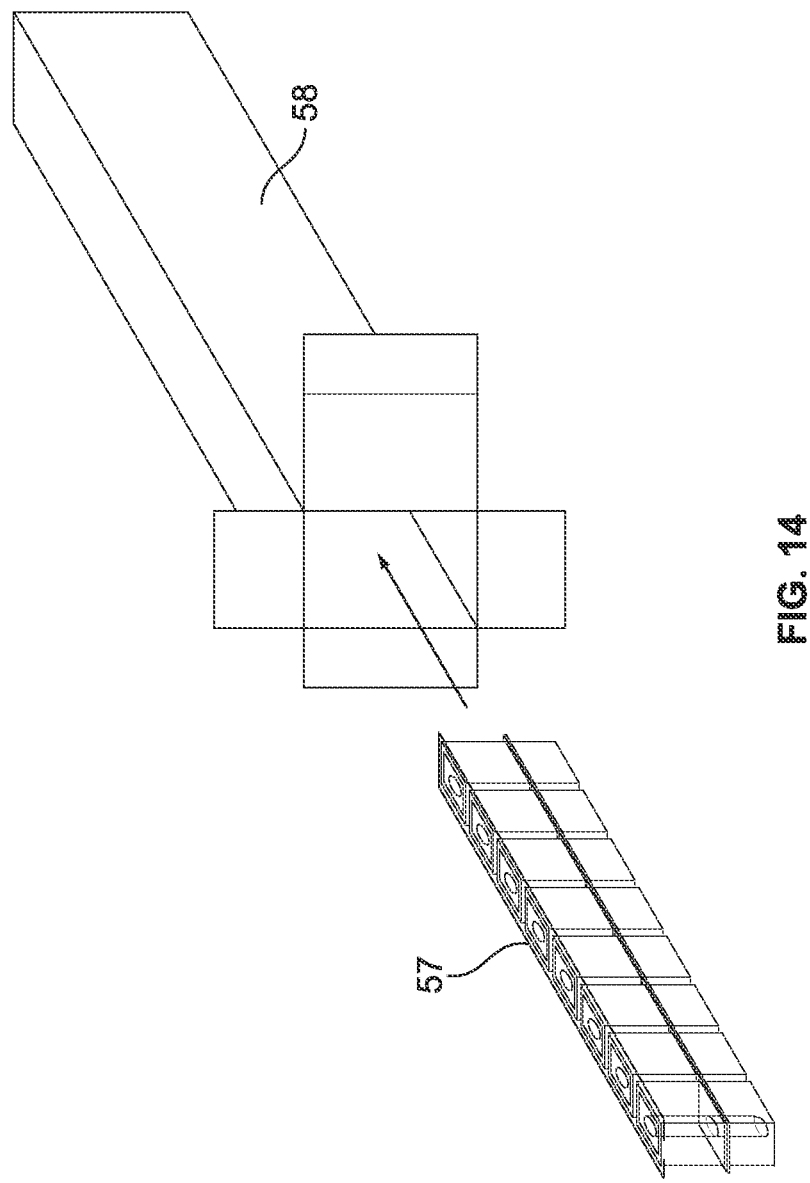
FIG. 14 illustrates the packaging of the partitioned components.

While moving through the clean room, FIG. 9 shows a portion of robotic filling apparatus 12 adding medicament 13 to each of the sub-assemblies 8. Preferably, filling is accomplished as a single step with each sub-assembly 8 being filled simultaneously. Centering member 6 ensures accuracy and efficiency in the filling process. In some cases, the medicament 13 could be already enclosed in a sealed vial or cartridge 60 and merely placed into the sub-assembly 8 as shown in FIG. 12. Once medicament 13 is added, a second medicated module sub-assembly 14 is fixed to the first sub-assembly 8 using robotic assembly equipment (not shown), as illustrated in FIG. 10. Again, preferably the second sub-assemblies 14 are fixed to the first sub-assemblies 8 simultaneously in a single step. The interior chamber of each receptacle 2 must be configured and/or sized to accommodate the connection of this second sub-assembly 14, which seals and finishes each of the medicated modules 9. In some cases, the interaction of the filling/assembly machine 12 with the medicated modules 9 from the bottom side of the tray 1 may become necessary to align parts for filling or assembly steps. In this case, the trays 1 can have open bottoms that are sealed later in the manufacturing process. Thus, bottom sealing surfaces can be present. Before leaving the clean room, the third and final seal 7 is added to aseptically enclose each of the receptacles 2 as illustrated in FIG. 11. Likewise, if a bottom seal is needed it will be fixed to the tray 1 before leaving the clean room. Once sealed, the grid 1 can be cut or partitioned along strike lines 3 or perforations 5 into smaller grids, for example a brick of 14 receptacles 2 or a row of 7 or any other user convenient amount that can then be directly commercially packaged for distribution to users. This is shown in FIGS. 13 and 14, where rows 57 are partitioned from tray 1 and then packaged in a box or carton 58 (FIG. 14). Prior to partitioning or packaging strike lines or perforations can be added to the final seal 7 to make removing individual receptacles 2 from the final smaller sized grids easier.

Alternatively, the interior chamber of the receptacles 2 could have a sealable open bottom portion. This might be needed to allow portions of the robotic filling apparatus 12 to support alignment of the first sub-assembly 8 with the filling nozzle or with the second sub-assembly 14 during filling and assembly steps on the automated filling and assembly line whilst remaining positioned in the receptacle 2. Whether sealed on the top or bottom or on both sides, labeling or other information can be directly applied to the final seal material as required.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A method of assembling multi-component medical products using sterile tray grids comprising the steps of:
   a. providing a packaging system comprising a sterile tray grid of at least two connected receptacles, wherein each receptacle is connected to an adjacent receptacle through a strike line which is configured to allow the receptacles to be removed and separated from one another, wherein each receptacle has a top sealing surface and an internal chamber having a centering member configured to support a first sub-assembly of a multi-component medical product, wherein the first sub-assembly is positioned on the centering member thereby fixing the first sub-assembly against rotational movement, and, wherein the packaging system is entirely contained within a first seal;
   b. removing the first seal in a sterile environment;
   c. connecting a second sub-assembly to the first sub-assembly to form a finished multi-component medical product while the centering member is holding the first sub-assembly in a predefined vertical position; and
   d. attaching a second seal to each of the top sealing surfaces of each receptacle to form a finished sterile tray grid of sealed receptacles, where each respective receptacle contains a respective multi-component medical product.

2. The method of claim 1, wherein a medicament is added to the first sub-assembly under sterile conditions prior to attaching the second seal.

3. The method of claim 2, wherein the finished multi-component medical product is a medicated module that contains a secondary medicament.

4. The method of claim 3, wherein the secondary medicament comprises a GLP-1 or a premix of insulin and a GLP-1.

5. The method of claim 3, wherein the medicated module is positioned on the centering member and is in the internal chamber.

6. The method of claim 1, wherein the second seal is perforated around each receptacle to form individual seals for each receptacle.

7. The method of claim 1, wherein the tray grid is partitioned into end user grids after the second seal is applied.

8. The method of claim 7, wherein the end user grids are individually packaged in commercial packaging.

9. The method of claim 1, wherein each receptacle has a folding edge that allows removal of the seal from the receptacle.

* * * * *